US008547464B2

(12) United States Patent
Kyushima et al.

(10) Patent No.: US 8,547,464 B2
(45) Date of Patent: *Oct. 1, 2013

(54) SOLID-STATE IMAGING DEVICE AND FRAME DATA CORRECTING METHOD WHICH DETERMINE A VOLTAGE VALUE CORRESPONDING TO A PIXEL PORTION IN FRAME DATA

(75) Inventors: Ryuji Kyushima, Hamamatsu (JP); Harumichi Mori, Hamamatsu (JP); Junichi Sawada, Hamamatsu (JP); Kazuki Fujita, Hamamatsu (JP); Masahiko Honda, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 133 days.

This patent is subject to a terminal disclaimer.

(21) Appl. No.: 12/864,134

(22) PCT Filed: Jan. 22, 2009

(86) PCT No.: PCT/JP2009/050971
§ 371 (c)(1),
(2), (4) Date: Jul. 22, 2010

(87) PCT Pub. No.: WO2009/093654
PCT Pub. Date: Jul. 30, 2009

(65) Prior Publication Data
US 2010/0295982 A1 Nov. 25, 2010

(30) Foreign Application Priority Data
Jan. 24, 2008 (JP) .................................. 2008-014030

(51) Int. Cl.
*H04N 5/335* (2011.01)
(52) U.S. Cl.
USPC ............ 348/308; 348/246; 348/294; 348/303

(58) Field of Classification Search
None
See application file for complete search history.

(56) References Cited

U.S. PATENT DOCUMENTS

| 6,118,846 A * | 9/2000 | Liu ................................. 378/62 |
| 6,396,539 B1 * | 5/2002 | Heller et al. .................. 348/246 |

(Continued)

FOREIGN PATENT DOCUMENTS

| CN | 1906925 | 1/2007 |
| DE | 198 60 036 | 3/2000 |

(Continued)

*Primary Examiner* — Roberto Velez
*Assistant Examiner* — Abdelaaziz Tissire
(74) *Attorney, Agent, or Firm* — Drinker Biddle & Reath LLP

(57) ABSTRACT

The present invention relates to a solid-state imaging device, etc., having a structure which enables to obtain an image with higher resolution by correcting pixel data even when any one of row selecting wirings is disconnected. A solid-state imaging device (1) comprises a photodetecting section (10), a signal reading-out section (20), a controlling section (30), and a correction processing section (40). The photodetecting section (10) has M×N pixel portions $P_{1,1}$ to $P_{M,N}$ two-dimensionally arrayed in M rows and N columns, and each of the pixel portions $P_{1,1}$ to $P_{M,N}$ includes a photodiode which generates charges of an amount corresponding to an incident light intensity and a reading-out switch connected to the photodiode. Charges generated in each of the pixel portions $P_{1,1}$ to $P_{M,N}$ are inputted into an integrating circuit $S_n$ through a reading-out wiring $L_{O,n}$. A voltage value outputted from the integrating circuit $S_n$ corresponding to the amount of inputted charges is outputted to an output wiring $L_{out}$ through a holding circuit $H_n$. The correction processing section (40) applies correction processing to frame data repeatedly outputted from the signal reading-out section (20), and then outputs the frame data after correction processing.

9 Claims, 6 Drawing Sheets

(56) References Cited

U.S. PATENT DOCUMENTS

| | | |
|---|---|---|
| 6,792,159 B1 | 9/2004 | Aufrichtig et al. |
| 6,961,088 B2 * | 11/2005 | Kameshima et al. ......... 348/303 |
| 6,995,373 B2 | 2/2006 | Ishii et al. |
| 7,106,371 B1 * | 9/2006 | Kubo et al. ................... 348/246 |
| 7,796,172 B1 | 9/2010 | Slagle et al. |
| 8,159,576 B2 | 4/2012 | Fujita et al. |
| 8,189,084 B2 | 5/2012 | Kyushima et al. |
| 2002/0085109 A1 | 7/2002 | Nakamura et al. |
| 2002/0105579 A1 * | 8/2002 | Levine et al. ................. 348/187 |
| 2002/0122123 A1 * | 9/2002 | Kimura ......................... 348/246 |
| 2002/0167601 A1 | 11/2002 | Ohzu et al. |
| 2003/0179125 A1 * | 9/2003 | Fujita et al. ................... 341/172 |
| 2005/0063513 A1 * | 3/2005 | Hsieh et al. .................. 378/98.8 |
| 2005/0145903 A1 | 7/2005 | Ishii et al. |
| 2006/0104417 A1 * | 5/2006 | Kameshima et al. ........... 378/98 |
| 2007/0096032 A1 * | 5/2007 | Yagi et al. ................ 250/370.11 |
| 2007/0252904 A1 | 11/2007 | Rosen |
| 2009/0295954 A1 * | 12/2009 | Mori et al. .................... 348/294 |
| 2010/0194937 A1 | 8/2010 | Kyushima et al. |
| 2010/0208113 A1 | 8/2010 | Kyushima et al. |
| 2010/0245646 A1 | 9/2010 | Fujita et al. |
| 2010/0295982 A1 | 11/2010 | Kyushima et al. |

FOREIGN PATENT DOCUMENTS

| | | |
|---|---|---|
| DE | 102 13 564 | 10/2003 |
| EP | 0 986 249 | 3/2000 |
| JP | 2000-46645 | 2/2000 |
| JP | 2000-324401 | 11/2000 |
| JP | 2001-251557 | 9/2001 |
| JP | 2003-296722 | 10/2003 |
| JP | 2004-521721 | 7/2004 |
| JP | 2005-210164 | 8/2005 |
| JP | 2006-211069 | 8/2006 |
| JP | 2006-234557 | 9/2006 |
| JP | 2007-174124 | 7/2007 |
| JP | 2008-252691 | 10/2008 |
| WO | WO 00/50879 | 8/2000 |
| WO | WO 2009/031585 | 3/2009 |

* cited by examiner

SOLID-STATE IMAGING DEVICE AND FRAME DATA CORRECTING METHOD WHICH DETERMINE A VOLTAGE VALUE CORRESPONDING TO A PIXEL PORTION IN FRAME DATA

TECHNICAL FIELD

The present invention relates to a solid-state imaging device comprising a plurality of photodetecting sections two-dimensionally arranged, and a frame data correcting method of correcting frame data outputted from the solid-state imaging device.

BACKGROUND ART

As a solid-state imaging device, those using the CMOS technique are known, and among these, a passive pixel sensor (PPS) type solid-state imaging device is known (see Patent Document 1). The PPS type solid-state imaging device has a structure in which PPS type pixel portions, each including a photodiode for generating charges of an amount corresponding to an incident light intensity, are two-dimensionally arrayed in M rows and N columns. In each pixel portion, charges generated in the photodiode in response to light incidence are accumulated in a capacitive element of an integrating circuit, and a voltage value corresponding to the accumulated charge amount is outputted.

In general, output terminals of M pixel portions belonging to each column are connected to an input terminal of an integrating circuit provided corresponding to the column via a reading-out wiring provided corresponding to the column. In order from the first row to the M-th row, charges generated in the photodiodes of the pixel portions are inputted into the corresponding integrating circuit via the corresponding reading-out wiring, and a voltage value corresponding to the amount of charges is outputted from the integrating circuit.

The N pixel portions belonging to each row are connected to a controlling section via a row selecting wiring provided corresponding to the row. According to a row selecting controlling signal transmitted from this controlling section via the row selecting wiring, the pixel portions output charges generated in the photodiodes to the reading-out wirings.

The PPS type solid-state imaging device is used for various purposes. For example, a PPS type solid-state imaging device is combined with a scintillator panel and used as an X-ray flat panel for a medical purpose or an industrial purpose. Further, a PPS type solid-state imaging device is used in an X-ray CT apparatus and a micro-focus X-ray inspection apparatus, etc. The solid-state imaging device to be used for these purposes includes a large-area photodetecting section including M×N pixel portions two-dimensionally arrayed, and the photodetecting section may be integrated on a semiconductor substrate each side of which has a length over 10 cm. Therefore, in some cases, only one solid-state imaging device is produced from one semiconductor wafer.

Patent Document 1: Japanese Laid-Open Patent Application No. 2006-234557

DISCLOSURE OF THE INVENTION

Problems that the Invention is to Solve

The present inventors have examined conventional solid-state imaging devices, and as a result, have discovered the following problems. That is, in a conventional solid-state imaging device, when a row selecting wiring corresponding to any one of the rows is disconnected in the middle of production, among N pixel portions belonging to this row, pixel portions positioned closer to the controlling section than the disconnection point are left connected to the controlling section by the row selecting wiring, however, the pixel portions farther from the controlling section than the disconnection point are disconnected from the controlling section.

Particularly, in a conventional solid-state imaging device, charges generated in photodiodes in response to light incidence in pixel portions positioned farther from the controlling section than the disconnection point are not reading-out to the integrating circuit, and are just accumulated in junction capacitance portions of the photodiodes. When the amount of charges accumulated in the junction capacitance portion of the photodiode exceeds a saturation level, charges over the saturation level overflow to the neighboring pixel portions.

Therefore, in a conventional solid-state imaging device, when one row selecting wiring is disconnected, this disconnection influences not only the pixel portions of the row connected to this row selecting wiring but also pixel portions of both rows neighboring the disconnected row, and eventually, pixel portions of consecutive three rows become defective lines.

On the other hand, when the defective lines are not consecutive and lines neighboring one defective line are normal lines, pixel data of the defective line can be interpolated by using pixel data of these neighboring normal lines. However, when pixel portions of consecutive three rows become defective lines, such interpolation is difficult. In particular, a solid-state imaging device having a photodetecting section with a large area as described above has a higher probability of disconnection due to long row selecting wirings.

In Patent Document 1 described above, an invention intended to solve this problem is proposed. That is, with the technique proposed in Patent Document 1, an average of all pixel data of a neighboring line neighboring a defective line and an average of all pixel data of further neighboring several normal lines are obtained. When a difference between these two averages is not less than a predetermined value, the neighboring line is also determined as defective and pixel data of the neighboring line is corrected, and further, based on the values after correction of the pixel data of the neighboring line, pixel data of the defective line is corrected.

In the technique proposed in Patent Document 1, when correcting the pixel data of the neighboring line determined as defective, an average of two pixel data on normal lines on both sides of and nearest the neighboring line is obtained, and this average is determined as pixel data of the neighboring line. When correcting the pixel data of the defective line, an average of two pixel data on neighboring lines on both sides of the defective line is obtained, and this average is determined as pixel data of the defective line.

However, in the technique proposed in Patent Document 1, processing of obtaining an average of two pixel data is repeated a plurality of times to correct pixel data of a defective line (and a line near the defective line and determined as defective), so that the resolution lowers near the defective line in a corrected image.

The present invention has been developed to eliminate the problems described above. It is an object of the present invention to provide a solid-state imaging device having a structure for making it possible to obtain an image with high resolution by properly correcting pixel data even when any one of the row selecting wirings disposed inside a photodetecting section is disconnected, and a frame data correcting method.

Means for Solving the Problems

A solid-state imaging device according to the present invention comprises: a photodetecting section including M×N pixel portions $P_{1,1}$ to $P_{M,N}$ two-dimensionally arrayed so as to constitute a matrix with M (integer not less than 2) rows and N (integer not less than 2) columns; a reading-out wiring $L_{O,n}$ connected to reading-out switches included in M pixel portions $P_{1,n}$ to $P_{M,n}$ belonging to the n(integer not less than 1 and not more than N)-th column in the photodetecting section; a signal reading-out section connected to the reading-out wirings $L_{O,1}$ to $L_{O,N}$, a controlling section controlling a voltage value output operation in the signal reading-out section by controlling opening and closing operations of the reading-out switches included in N pixel portions $P_{m,1}$ to $P_{m,N}$ belonging to the m(integer not less than 1 and not more than M)-th row in the photodetecting section; and a row selecting wiring $L_{V,m}$ connected to reading-out switches included in N pixel portions $P_{m,1}$ to $P_{m,N}$ belonging to the m-th row in the photodetecting section. The photodetecting section, the reading-out wiring $L_{O,n}$, the signal reading-out section, the controlling section, and the row selecting wiring $L_{V,m}$ constitute one sensor element.

In each photodetecting section, each of the pixel portions $P_{1,1}$ to $P_{M,N}$ includes a photodiode which generates charges of an amount corresponding to an incident light intensity, and a reading-out switch connected to the photodiode. The reading-out wiring $L_{O,n}$ reads out charges generated in a photodiode included in any one of the pixel portions $P_{1,n}$ to $P_{M,n}$ via a corresponding reading-out switch. The signal reading-out section temporarily holds voltage values corresponding to the amounts of charges inputted through the reading-out wirings $L_{O,n}$, and then successively outputs the held voltage values. The controlling section makes the signal reading-out section repeatedly output the voltage values corresponding to the amounts of charges generated in the photodiodes included in the M×N pixel portions $P_{1,1}$ to $P_{M,N}$ in the photodetecting section as frame data. The row selecting wiring $L_{V,m}$ transmits a signal for controlling opening and closing operations of these reading-out switches from the controlling section to the reading-out switches.

The solid-state imaging device according to the present invention comprises a correction processing section in addition to the above-described photodetecting section, reading-out wirings $L_{O,n}$, signal reading-out section, controlling section, and row selecting wirings $L_{V,m}$. The correction processing section performs correction processing by acquiring frame data repeatedly outputted from the signal reading-out section. The frame data correcting method according to the present invention is for correcting frame data to be outputted from the solid-state imaging device (solid-state imaging device according to the present invention) having the above-described structure.

In particular, the correction processing section of the solid-state imaging device according to the present invention carries out the frame correcting method according to the present invention. Particularly, when a pixel portion disconnected from the controlling section due to disconnection of the m1(integer not less than 1 and not more than M)-th row selecting wiring $L_{V,m1}$ of the row selecting wirings $L_{V,1}$ to $L_{V,M}$ is defined as a pixel portion $P_{m1,n1}$ (n1 is an integer not less than 1 and not more than N), and a pixel portion neighboring the pixel portion $P_{m1,n1}$ and belonging to the m2(integer not less than 1 and not more than M)-th row neighboring the m1-th row is defined as a pixel portion $P_{m2,n1}$, the correction processing section corrects a voltage value corresponding to the pixel portion $P_{m2,n1}$ in frame data outputted from the signal reading-out section by converting the voltage value in accordance with a function expression with the voltage value as an input variable, and determines a voltage value corresponding to the pixel portion $P_{m1,n1}$ in the frame data based on the corrected value of the voltage value corresponding to the pixel portion $P_{m2,n1}$.

Thus, in accordance with the correction processing section of the solid-state imaging device and the frame data correcting method, when correcting a voltage value corresponding to the pixel portion $P_{m2,n1}$ on the m2-th row selecting wiring $L_{V,m2}$ neighboring the disconnected m1-th row selecting wiring $L_{V,m1}$, it is not necessary to use a voltage value corresponding to the pixel portion on a normal line. Therefore, in comparison with the technique described in Patent Document 1, the resolution near a defective line in an image after correction becomes higher in the present invention.

Preferably, the correction processing section of the solid-state imaging device according to the present invention (frame data correcting method according to the present invention) uses a polynomial as the function expression. In this case, preferably, the correction processing section uses values determined based on incident light intensity dependencies of voltage values corresponding to a pixel portion which is neither the pixel portion $P_{m1,n1}$ nor the pixel portion $P_{m2,n1}$ and incident light intensity dependencies of voltage values corresponding to the pixel portion $P_{m2,n1}$, as coefficients of the polynomial.

Preferably, the correction processing section of the solid-state imaging device according to the present invention (the frame data correcting method according to the present invention) corrects a voltage value corresponding to a pixel portion $P_{m2,n1}$ in frame data by setting the coefficients for each of any plurality of row selecting wirings among the row selecting wirings $L_{V,1}$ to $L_{V,M}$ when the plurality of row selecting wirings are disconnected.

The solid-state imaging device according to the present invention may comprise a plurality of sensor elements each having the same structure as that of a sensor element consisting of the above-described photodetecting section, reading-out wirings $L_{O,n}$, signal reading-out section, and row selecting wirings $L_{V,m}$. In this case, preferably, when any one of row selecting wirings included in any one of the plurality of sensor elements is disconnected, the correction processing section of the solid-state imaging device according to the present invention (frame data correcting method according to the present invention) uses coefficients obtained based on incident light intensity dependencies of voltage values corresponding to a pixel portion which is neither a pixel portion $P_{m1,n1}$ nor a pixel portion $P_{m2,n1}$ and incident light intensity dependencies of voltage values corresponding to the pixel portion $P_{m2,n1}$. The correction coefficients are set in advance based on incident light intensity dependencies of voltage outputs of "normal pixel" and "neighboring pixel" measured in an inspection before use of the product.

An X-ray CT apparatus according to the present invention includes an X-ray output section, a solid-state imaging device having the above-described structure (solid-state imaging device according to the present invention), moving means, and an image analyzing section. The X-ray output section outputs X-rays to a subject. The solid-state imaging device images a subject by receiving X-rays reaching through the subject from the X-ray output section. The moving means moves the X-ray output section and the solid-state imaging device relative to the subject. The image analyzing section inputs frame data after correction processing outputted from the solid-state imaging device, and generates a tomographic image of the subject based on the frame data.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the scope of the invention will be apparent to those skilled in the art from this detailed description.

Effects of the Invention

In accordance with the solid-state imaging device and frame data correcting method according to the present invention, even when any one of the row selecting wirings is disconnected, an image with high resolution can be obtained by properly correcting pixel data.

Figure 1:
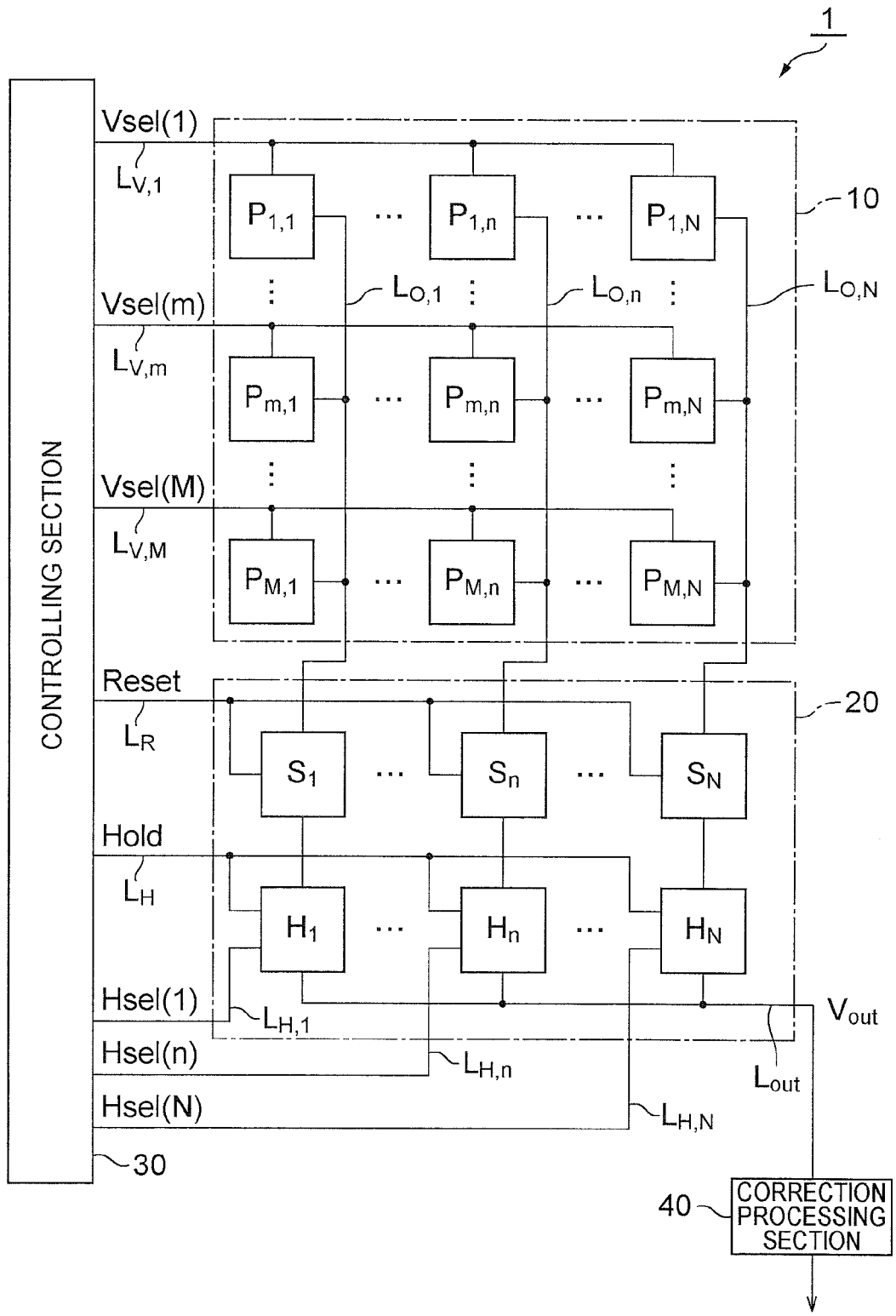
FIG. 1 is a view showing a configuration of a first embodiment of a solid-state imaging device according to the present invention.

DESCRIPTION OF THE REFERENCE NUMERALS 1, 2: solid-state imaging device; 10, 10A, 10B: photodetecting section; 20, 20A, 20B: signal reading-out section; 30: controlling section; 40: correction processing section; $P_{1,1}$ to $P_{M,N}$: pixel portion; PD: photodiode; $SW_1$: reading-out switch; $S_1$ to $S_N$: integrating circuit; $C_2$: integrating capacitive element; $SW_2$: discharge switch; $A_2$: amplifier; $H_1$ to $H_N$: holding circuit; $C_3$: holding capacitive element; $SW_{31}$: input switch; $SW_{32}$: output switch; $L_{V,m}$: m-th row selecting wiring; $L_{H,n}$: n-th column selecting wiring; $L_{O,n}$: n-th column reading-out wiring; $L_R$: discharge controlling wiring; $L_H$: hold controlling wiring; $L_{out}$: voltage output wiring.

BEST MODES FOR CARRYING OUT THE INVENTION

In the following, embodiments of a solid-state imaging device and a frame data correcting method according to the present invention will be explained in detail with reference to FIGS. 1 to 6. In the description of the drawings, identical or corresponding components are designated by the same reference numerals, and overlapping description is omitted.

First Embodiment

FIG. 1 is a view showing a configuration of a first embodiment of a solid-state imaging device according to the present invention. The solid-state imaging device 1 according to the first embodiment comprises a photodetecting section 10, a signal reading-out section 20, a controlling section 30, and a correction processing section 40. When it is used as an X-ray flat panel, a scintillator panel is overlaid on the photodetecting surface 10 of the solid-state imaging device 1.

The photodetecting section 10 includes M×N pixel portions $P_{1,1}$ to $P_{M,N}$ two-dimensionally arrayed on a matrix of M rows and N columns. The pixel portion $P_{m,n}$ shows a pixel portion on the m-th row in the n-th column. Here, M and N are integers not less than 2, m is an integer not less than 1 and not more than M, and n is an integer nor less than 1 and not more than N. The pixel portions $P_{m,n}$ are a PPS type, and have a common configuration.

N pixel portions $P_{m,1}$ to $P_{m,N}$ belonging to the m-th row are connected to the controlling section 30 via an m-th row selecting wiring $L_{V,m}$. Output terminals of M pixel portions $P_{1,n}$ to $P_{M,n}$ belonging to the n-th column are connected to the integrating circuit $S_n$ included in the signal reading-out section 20 via an n-th column reading-out wiring $L_{O,n}$.

The signal reading-out section 20 includes N integrating circuits $S_1$ to $S_N$ and N holding circuits $H_1$ to $H_N$. The integrating circuits $S_n$ have a common configuration. The holding circuits $H_n$ have a common configuration.

Each integrating circuit $S_n$ has an input terminal connected to the reading-out wiring $L_{O,n}$, and temporarily accumulates charges inputted in the input terminal and then outputs a voltage value corresponding to the accumulated charge amount from an output terminal to the holding circuit $H_n$. N integrating circuits $S_1$ to $S_N$ are connected to the controlling section 30 by a discharge controlling wiring $L_R$.

Each holding circuit $H_n$ has an input terminal connected to the output terminal of the integrating circuit $S_n$, and temporarily holds a voltage value inputted in the input terminal and outputs the held voltage value from an output terminal to the output wiring $L_{out}$. N holding circuits $H_1$ to $H_N$ are connected to the controlling section 30 via a hold controlling wiring $L_H$. Each holding circuit $H_n$ is connected to the controlling section 30 via an n-th column selecting wiring $L_{H,n}$.

The controlling section 30 outputs an m-th row selecting controlling signal Vsel(m) to the m-th row selecting wiring $L_{V,m}$ to supply this m-th row selecting controlling signal Vsel(m) to N pixel portions $P_{m,1}$ to $P_{m,N}$ belonging to the m-th row. M row selecting controlling signals Vsel(1) to Vsel(M) are successively set to significant values. For successively setting M row selecting controlling signals Vsel(1) to Vsel(M) to significant values and outputting these, the controlling section 30 includes a shift register.

The controlling section 30 outputs an n-th column selecting controlling signal Hsel(n) to the n-th column selecting wiring $L_{H,n}$ to supply this n-th column selecting controlling signal Hsel(n) to the holding circuit $H_n$. N column selecting controlling signals Hsel(1) to Hsel(N) are also successively set to significant values. For successively setting N column selecting controlling signals Hsel(1) to Hsel(N) to significant values and outputting these, the controlling section 30 includes a shift register.

The controlling section 30 outputs a discharge controlling signal Reset to the discharge controlling wiring $L_R$ to supply this discharge controlling signal Reset to the N integrating circuits $S_1$ to $S_N$. The controlling section 30 outputs a hold controlling signal Hold to the hold controlling wiring $L_H$ to supply this hold controlling signal Hold to the N holding circuits $H_1$ to $H_N$.

As described above, the controlling section 30 controls opening and closing operations of the reading-out switches $SW_1$ included in N pixel portions $P_{m,1}$ to $P_{m,N}$ belonging to the m-th row in the photodetecting section 10, and controls voltage value holding operations and voltage value output operations in the signal reading-out section 20. Accordingly, the controlling section 30 makes the signal reading-out section 20 repeatedly output voltage values corresponding to amounts of charges generated in photodiodes PD included in the M×N pixel portions $P_{1,1}$ to $P_{M,N}$ in the photodetecting section 10 as frame data.

The correction processing section 40 acquires frame data repeatedly outputted from the signal reading-out section 20, applies correction processing to the frame data, and then outputs the frame data after correction processing. Details of the correction processing in the correction processing section 40 will be described in detail later.

Figure 2:
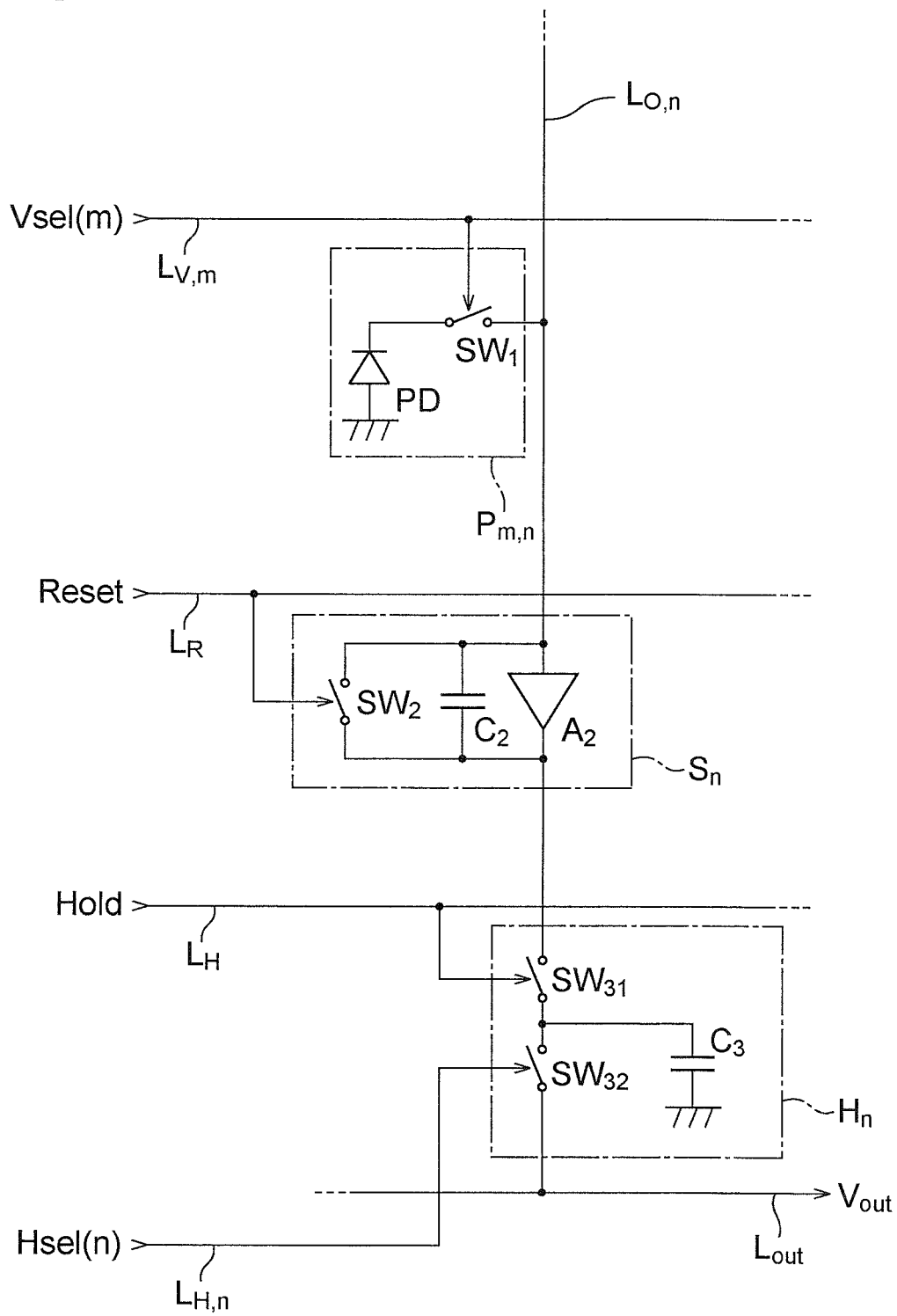
FIG. 2 is a circuit diagram of a pixel portion $P_{m,n}$, an integrating circuit $S_n$, and a holding circuit $H_n$ included in the solid-state imaging device according to the first embodiment.

FIG. 2 is a circuit diagram of a pixel portion $P_{m,n}$, an integrating circuit $S_n$, and a holding circuit $H_n$ included in the solid-state imaging device according to the first embodiment. In FIG. 2, circuit diagrams of a pixel portion $P_{m,n}$ as a representative of the M×N pixel portions $P_{1,1}$ to $P_{M,N}$, an integrating circuit $S_n$ as a representative of the N integrating circuits $S_1$ to $S_N$, and a holding circuit $H_n$ as a representative of the N holding circuits $H_1$ to $H_N$ are shown. That is, circuit portions concerning a pixel portion $P_{m,n}$ on the m-th row in the n-th column and the n-th column reading-out wiring $L_{O,n}$ are shown in FIG. 2.

The pixel portion $P_{m,n}$ includes a photodiode PD and a reading-out switch $SW_1$. The anode terminal of the photodiode PD is grounded, and the cathode terminal of the photodiode PD is connected to the n-th column reading-out wiring $L_{O,n}$ via the reading-out switch $SW_1$. The photodiode PD generates charges of an amount corresponding to an incident light intensity, and the generated charges are accumulated in a junction capacitance portion. The reading-out switch $SW_1$ is supplied with an m-th row selecting controlling signal which passed through the m-th row selecting wiring $L_{V,m}$ from the controlling section 30. The m-th row selecting controlling signal is an electric signal which instructs opening and closing operations of the reading-out switches $SW_1$ included in N pixel portions $P_{m,1}$ to $P_{m,N}$ belonging to the m-th row in the photodetecting section 10.

In the pixel portion $P_{m,n}$, when the m-th row selecting controlling signal Vsel(m) is at low level, the reading-out switch $SW_1$ opens. In this case, charges generated in the photodiode PD are not outputted to the n-th column reading-out wiring $L_{O,n}$ but are accumulated in the junction capacitance portion. On the other hand, when the m-th row selecting controlling signal Vsel(m) is at high level, the reading-out switch $SW_1$ closes. In this case, charges generated in the photodiode PD and accumulated in the junction capacitance portion until then are outputted to the n-th column reading-out wiring $L_{O,n}$ through the reading-out switch $SW_1$.

The n-th column reading-out wiring $L_{O,n}$ is connected to the reading-out switches $SW_1$ included in M pixel portions $P_{1,n}$ to $P_{M,n}$ belonging to the n-th column in the photodetecting section 10. The n-th column reading-out wiring $L_{O,n}$ reads out charges generated in the photodiode PD included in any one of the M pixel portions $P_{1,n}$ to $P_{M,n}$ via the reading-out switch $SW_1$ included in the pixel portion and transfers the charges to the integrating circuit $S_n$.

The integrating circuit $S_n$ includes an amplifier $A_2$, an integrating capacitive element $C_2$, and a discharge switch $SW_2$. The integrating capacitive element $C_2$ and the discharge switch $SW_2$ are connected in parallel to each other, and provided between an input terminal and an output terminal of the amplifier $A_2$. The input terminal of the amplifier $A_2$ is connected to the n-th column reading-out wiring $L_{O,n}$. The discharge switch $SW_2$ is supplied with a discharge controlling signal Reset which passed through the discharge controlling wiring $L_R$ from the controlling section 30. The discharge controlling signal Reset is an electric signal which instructs opening and closing operations of the discharge switches $SW_2$ included in N integrating circuits $S_1$ to $S_N$.

In the integrating circuit $S_n$, when the discharge controlling signal Reset is at high level, the discharge switch $SW_2$ closes. In this case, the integrating capacitive element $C_2$ is discharged, and accordingly, a voltage value to be outputted from the integrating circuit $S_n$ is initialized. When the discharge controlling signal Reset is at low level, the discharge switch $SW_2$ opens. In this case, charges inputted in the input terminal are accumulated in the integrating capacitive element $C_2$, and a voltage value corresponding to the accumulated charge amount is outputted from the integrating circuit $S_n$.

The holding circuit $H_n$ includes an input switch $SW_{31}$, an output switch $SW_{32}$, and a holding capacitive element $C_3$. One end of the holding capacitive element $C_3$ is grounded. The other end of the holding capacitive element $C_3$ is connected to the output terminal of the integrating circuit $S_n$ via the input switch $SW_{31}$, and connected to the voltage output wiring $L_{out}$ via the output switch $SW_{32}$. The input switch $SW_{31}$ is supplied with a hold controlling signal Hold which passed through the hold controlling wiring $L_H$ from the controlling section 30. The hold controlling signal Hold is an electric signal which instructs opening and closing operations of input switches $SW_{31}$ included in the N holding circuits $H_1$ to $H_N$. The output switch $S_{32}$ is supplied with an n-th column selecting controlling signal Hsel(n) which passed through the n-th column selecting wiring $L_{H,n}$ from the controlling section 30. The n-th column selecting controlling signal Hsel(n) is an electric signal which instructs opening and closing operations of the output switch $SW_{32}$ included in the holding circuit $H_n$.

In this holding circuit $H_n$, when the hold controlling signal Hold switches from high level to low level, the input switch $SW_{31}$ switches from a closed state to an open state, and a voltage value inputted in the input terminal at this time is held by the holding capacitive element $C_3$. When the n-th column selecting controlling signal Hsel(n) is at high level, the output switch $SW_{32}$ closes. In this case, the voltage value held by the holding capacitive element $C_3$ is outputted to the voltage output wiring $L_{out}$.

When outputting voltage values corresponding to received light intensities in the N pixel portions $P_{m,1}$ to $P_{m,N}$ belonging to the m-th row in the photodetecting section 10, the controlling section 30 instructs temporary closing and then opening of the discharge switches $SW_2$ included in the N integrating circuits $S_1$ to $S_N$ by a discharge controlling signal Reset. Thereafter, the controlling section 30 instructs closing of the reading-out switches $SW_1$ included in the N pixel portions $P_{m,1}$ to $P_{m,N}$ of the m-th row in the photodetecting section 10 for a predetermined period by an m-th row selecting controlling signal Vsel(m). In the predetermined period, the controlling section 30 instructs switching of the input switches $SW_{31}$ included in the N holding circuits $H_1$ to $H_N$ from a closed state to an open state by a hold controlling signal Hold. Then, after the predetermined period, the controlling section 30 instructs successive closing of the output switches $SW_{32}$ included in the N holding circuits $H_1$ to $H_N$ for a predetermined period by column selecting controlling signals Hsel(1) to Hsel(N). The controlling section 30 performs the above-described control for the rows in order.

Next, operations of the solid-state imaging device 1 according to the first embodiment will be described. In the solid-state imaging device 1 according to the first embodiment, under control by the controlling section 30, the M row selecting controlling signals Vsel(1) to Vsel(M), the N column selecting controlling signals Hsel(1) to Hsel(N), the discharge controlling signal Reset, and the hold controlling signal Hold change their levels at predetermined timings. Accordingly, light made incident on the photodetecting surface 10 can be imaged and frame data can be obtained, and further, the frame data can be corrected by the correction processing section 40.

Figure 3:
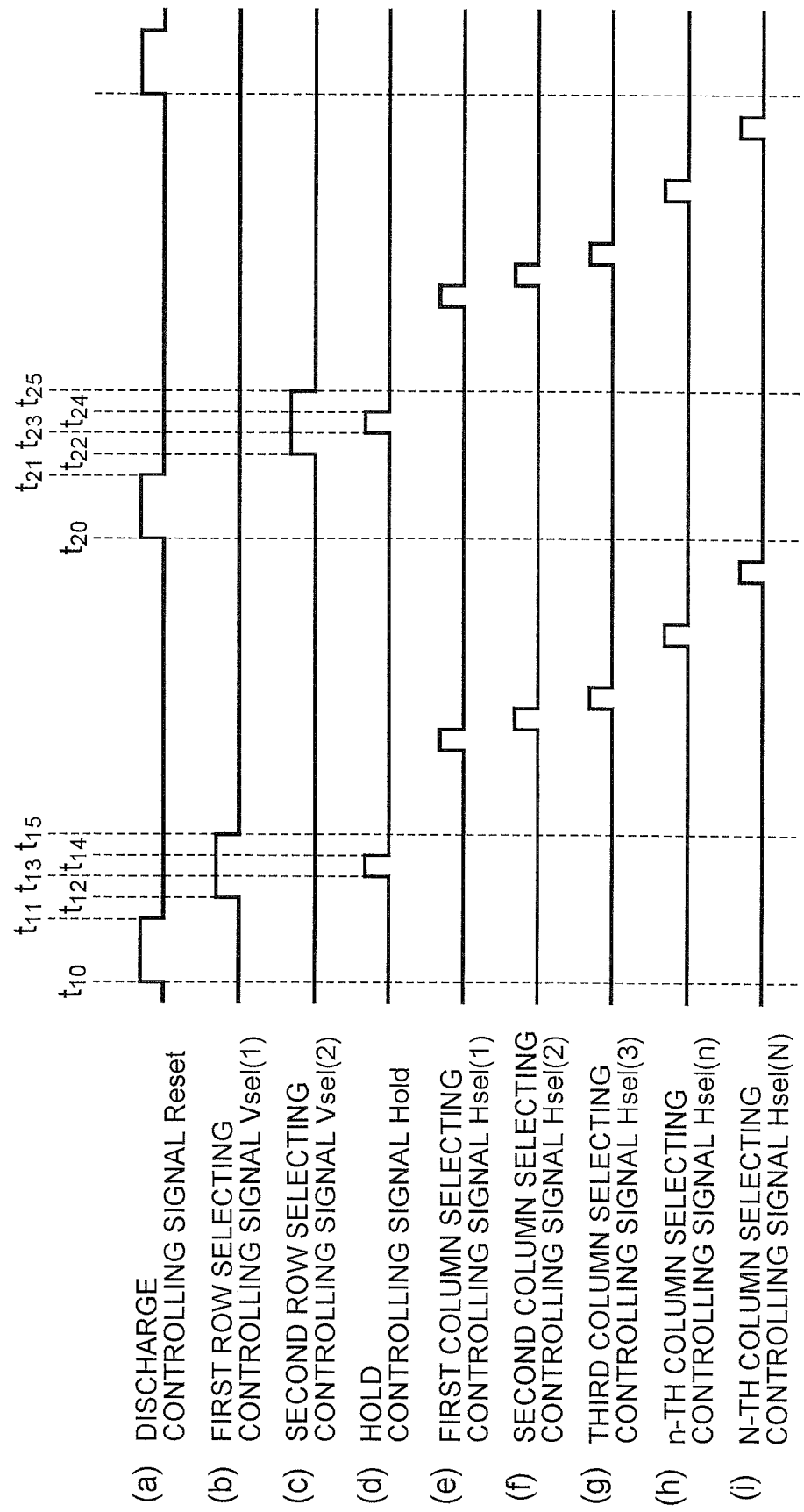
FIG. 3 is a timing chart for describing operations of the solid-state imaging device according to the first embodiment.

FIG. 3 is a timing chart describing operations of the solid state imaging device according to the first embodiment. FIG. 3 shows (a) the discharge controlling signal Reset for instructing opening and closing operations of the discharge switches $SW_2$ included in the N integrating circuits $S_1$ to $S_N$, (b) the first row selecting controlling signal Vsel(1) for instructing opening and closing operations of the reading-out switches $SW_1$ included in the N pixel portions $P_{1,1}$ to $P_{1,N}$ belonging to the first row in the photodetecting section 10, (c) the second row selecting controlling signal Vsel(2) for instructing opening and closing operations of the reading-out switches $SW_1$ included in the N pixel portions $P_{2,1}$ to $P_{2,N}$ belonging to the second row in the photodetecting section 10, and (d) the hold controlling signal Hold for instructing opening and closing operations of the input switches $SW_{31}$ included in the N holding circuits $H_1$ to $H_N$.

FIG. 3 further subsequently shows (e) the first column selecting controlling signal Hsel(1) for instructing opening and closing operations of the output switch $SW_{32}$ included in the holding circuit $H_1$, (f) the second column selecting controlling signal Hsel(2) for instructing opening and closing operations of the output switch $SW_{32}$ included in the holding circuit $H_2$, (g) the third column selecting controlling signal Hsel(3) for instructing opening and closing operations of the output switch $SW_{32}$ included in the holding circuit $H_3$, (h) the n-th column selecting controlling signal Hsel(n) for instructing opening and closing operations of the output switch $SW_{32}$ included in the holding circuit $H_n$, and (i) the N-th column selecting controlling signal Hsel(N) for instructing opening and closing operations of the output switch $SW_{32}$ included in the holding circuit $H_N$.

Charges generated in the photodiodes PD included in the N pixel portions $P_{1,1}$ to $P_{1,N}$ belonging to the first row and accumulated in the junction capacitance portions are reading-out as follows.

That is, before the time $t_{10}$, the M row selecting controlling signals Vsel(1) to Vsel(M), the N column selecting controlling signals Hsel(1) to Hsel(N), the discharge controlling signal Reset, and the hold controlling signal Hold are at low level. During a period from the time $t_{10}$ to $t_{11}$, the discharge controlling signal Reset to be outputted from the controlling section 30 to the discharge controlling wiring $L_R$ becomes high level, and accordingly, in the N integrating circuits $S_1$ to $S_N$, the discharge switches $SW_2$ close and the integrating capacitive elements $C_2$ are discharged. During a period from the time $t_{12}$ after the time $t_{11}$ to the time $t_{15}$, the first row selecting controlling signal Vsel(1) to be outputted from the controlling section 30 to the first row selecting wiring $L_{V,1}$ becomes high level, and accordingly, the reading-out switches $SW_1$ included in the N pixel portions $P_{1,1}$ to $P_{1,N}$ belonging to the first row in the photodetecting section 10 close.

In the period ($t_{12}$ to $t_{15}$), during the period from the time $t_{13}$ to the time $t_{14}$, the hold controlling signal Hold to be outputted from the controlling section 30 to the hold controlling wiring $L_H$ becomes high level, and accordingly, input switches $SW_{31}$ in the N holding circuits $H_1$ to $H_N$ close.

In the period ($t_{12}$ to $t_{15}$), the reading-out switch $SW_1$ included in each pixel portion $P_{1,n}$ belonging to the first row is closed and the discharge switch $SW_2$ of each integrating circuit $S_n$ is open. Therefore, charges generated in the photodiode PD of each pixel portion $P_{1,n}$ and accumulated in the junction capacitance portion until then are transferred to the integrating capacitive element $C_2$ (accumulated in the integrating capacitive element $C_2$) of the integrating circuit $S_n$ through the reading-out switch $SW_1$ of the pixel portion $P_{1,n}$ and the n-th column reading-out wiring $L_{O,n}$. Then, a voltage value corresponding to the amount of charges accumulated in the integrating capacitive element $C_2$ of each integrating circuit $S_n$ is outputted from the output terminal of the integrating circuit $S_n$.

At the time $t_{14}$ in the period ($t_{12}$ to $t_{15}$), the hold controlling signal Hold switches from high level to low level, and accordingly, in each of the N holding circuits $H_1$ to $H_N$, the input switch $SW_{31}$ switches from a closed state to an open state. A voltage value outputted from the output terminal of the integrating circuit $S_n$ and inputted in the input terminal of the holding circuit $H_n$ at this time is held by the holding capacitive element $C_3$.

Then, after the period ($t_{12}$ to $t_{15}$), column selecting controlling signals Hsel(1) to Hsel(N) to be outputted from the controlling section 30 to the column selecting wirings $L_{H,1}$ to $L_{H,N}$ successively become high level for a predetermined period. Accordingly, the output switches $SW_{32}$ included in the N holding circuits $H_1$ to $H_N$ successively close for the predetermined period. At this time, the voltage values held in the holding capacitive elements $C_3$ of the holding circuits $H_n$ are successively outputted to the voltage output wiring $L_{out}$ through the output switches $SW_{32}$. The voltage values $V_{out}$ to be outputted to the voltage output wiring $L_{out}$ indicate the received light intensities received by the photodiodes PD included in the N pixel portions $P_{1,1}$ to $P_{1,N}$ belonging to the first row. The voltage values $V_{out}$ to be outputted from the N holding circuits $H_1$ to $H_N$ to the voltage output wiring $L_{out}$ are inputted into the correction processing section 40 through the voltage output wiring $L_{out}$.

Subsequently, charges generated in the photodiodes PD included in N pixel portions $P_{2,1}$ to $P_{2,N}$ belonging to the second row and accumulated in the junction capacitance portions are reading-out as follows.

Particularly, during the period from the time $t_{20}$ to the time $t_{21}$, the discharge controlling signal Reset to be outputted from the controlling section 30 to the discharge controlling wiring $L_R$ becomes high level. Accordingly, in the N integrating circuits $S_1$ to $S_N$, the discharge switches $SW_2$ close and the integrating capacitive elements $C_2$ are discharged. During the period from the time $t_{22}$ after the time $t_{21}$ to the time $t_{25}$, the second row selecting controlling signal Vsel(2) to be outputted from the controlling section 30 to the second row selecting wiring $L_{V,2}$ becomes high level, and accordingly, the reading-out switches $SW_1$ included in the N pixel portions $P_{2,1}$ to $P_{2,N}$ belonging to the second row in the photodetecting section 10 close.

In the period ($t_{22}$ to $t_{25}$), during the period from the time $t_{23}$ to the time $t_{24}$, the hold controlling signal Hold to be outputted from the controlling section 30 to the hold controlling wiring $L_H$ becomes high level. Accordingly, input switches $SW_{31}$ in the N holding circuits $H_1$ to $H_N$ close.

Then, after the period ($t_{22}$ to $t_{25}$), column selecting controlling signals Hsel(1) to Hsel(N) to be outputted from the controlling section 30 to the column selecting wirings $L_{H,1}$ to $L_{H,N}$ successively become high level for a predetermined period. Accordingly, the output switches $SW_{32}$ included in the N holding circuits $H_1$ to $H_N$ successively close for the predetermined period.

Thus, voltage values $V_{out}$ indicating received light intensities received by the photodiodes PD included in the N pixel portions $P_{2,1}$ to $P_{2,N}$ belonging to the second row are outputted to the voltage output wiring $L_{out}$. The voltage values $V_{out}$ outputted from the N holding circuits $H_1$ to $H_N$ to the voltage output wiring $L_{out}$ are inputted into the correction processing section 40 through the voltage output wiring $L_{out}$.

Subsequent to the above-described operation for the first row and the second row, the same operation is performed for the third to the M-th rows, and accordingly, frame data showing an image to be obtained by one imaging is obtained. When the operation for the M-th row is finished, the same operation is performed again in order from the first row, and accordingly, frame data showing the next image is obtained. By thus repeating the same operation with a predetermined period, voltage values $V_{out}$ indicating two-dimensional intensity distribution of an image of light received by the photodetecting section 10 are outputted to the voltage output wiring $L_{out}$ (frame data is repeatedly obtained). These frame data is inputted into the correction processing section 40.

In the period during which the reading-out switches $SW_1$ included in the N pixel portions $P_{m,1}$ to $P_{m,N}$ belonging to the m-th row are closed, charges generated in the photodiode PD of each pixel portion $P_{m,n}$ belonging to the m-th row and accumulated in the junction capacitance portion are transferred to the integrating capacitive element $C_2$ of the integrating circuit $S_n$ through the reading-out switch $SW_1$ of the pixel portion $P_{m,n}$ and the n-th column reading-out wiring $L_{O,n}$. At this time, the accumulated charges in the junction capacitance portion of the photodiode PD of each pixel portion $P_{m,n}$ of the m-th row are initialized.

However, when a certain m-th row selecting wiring $L_{V,m}$ is disconnected at a point halfway, the m-th row selecting controlling signal Vsel(m) is not transmitted to pixel portions farther from the controlling section 30 than the disconnection point among N pixel portions $P_{m,1}$ to $P_{m,N}$ belonging to the m-th column. Therefore, in the pixel portion influenced by the disconnection, the reading-out switch $SW_1$ is left open, and charges cannot be transferred to the integrating circuit $S_n$. Particularly, in pixel portions which are influenced by the disconnection, initialization of the accumulated charges in the junction capacitance portions of the photodiode PD by the charge transfer is impossible. In the condition that this state continues, charges generated in the photodiode in response to light incidence in the pixel portion which is influenced by disconnection are only accumulated in the junction capacitance portion of the photodiode. In the case that the charges exceed the saturation level, the charges overflow to the pixel portions on both neighboring rows, and defective lines occur in pixel portions on consecutive three rows.

Therefore, in the solid-state imaging device 1 according to the first embodiment, the correction processing section 40 acquires frame data repeatedly outputted from the signal reading-out section 20, and applies the following correction processing (frame data correcting method according to the present invention) to each of the acquired frame data.

As a precondition for the following description, it is assumed that an m1-th row selecting wiring $L_{V,m1}$ which is any one of the row selecting wirings $L_{V,1}$ to $L_{V,M}$ is disconnected. A pixel portion on a defective line disconnected from the controlling section 30 due to disconnection of the m1-th row selecting wiring $L_{V,11}$ among N pixel portions $P_{m1,1}$ to $P_{m1,N}$ belonging to the m1-th row is defined as a pixel portion $P_{m1,n1}$. A pixel portion on a neighboring line which belongs to the m2-th row neighboring the m1-th row and neighbors the pixel portion $P_{m1,n1}$ is defined as a pixel portion $P_{m2,n1}$. Here, m1 and m2 are integers not less than 1 and not more than M, n1 is an integer not less than 1 and not more than N, and the difference between m1 and m2 is 1.

The correction processing section 40 corrects a voltage value corresponding to a pixel portion $P_{m2,n1}$ in frame data outputted from the signal reading-out section 20 by converting the voltage value according to a function expression containing the voltage value as an input variable. At this time, the correction processing section 40 can use an arbitrary relational expression as the above-described function expression, however, use of a polynomial is convenient. The correction processing section 40 can use values determined based on incident light intensity dependencies of voltage values corresponding to a pixel portion which is neither a pixel portion $P_{m1,n1}$ nor a pixel portion $P_{m2,n1}$ and incident light intensity dependencies of voltage values corresponding to the pixel portion $P_{m2,n1}$ as coefficients of the polynomial.

It is also preferable that the correction processing section 40 corrects a voltage value corresponding to a pixel portion $P_{m2,n1}$ in frame data by setting the coefficients for each of any plurality of row selecting wirings among the row selecting wirings $L_{V,1}$ to $L_{V,M}$ when the plurality of row selecting wirings are disconnected.

Further, the correction processing section 40 determines a voltage value corresponding to the pixel portion $P_{m1,n1}$ on the defective line in the frame data based on the value after correction of the voltage value corresponding to the pixel portion $P_{m2,n1}$ on the neighboring line. Preferably, this determination is made by interpolation based on voltage values corresponding to pixel portions $P_{m2,n1}$ on neighboring lines on both sides of the defective line.

The correction processing section 40 corrects voltage values corresponding to the pixel portions $P_{m2,n1}$ on the neighboring lines and the pixel portion $P_{m1,n1}$ on the defective line were corrected as described above, and then outputs the frame data after correction processing.

Correction processing for the voltage value corresponding to the pixel portion $P_{m2,n1}$ on the neighboring line is described in detail below.

Figure 4:
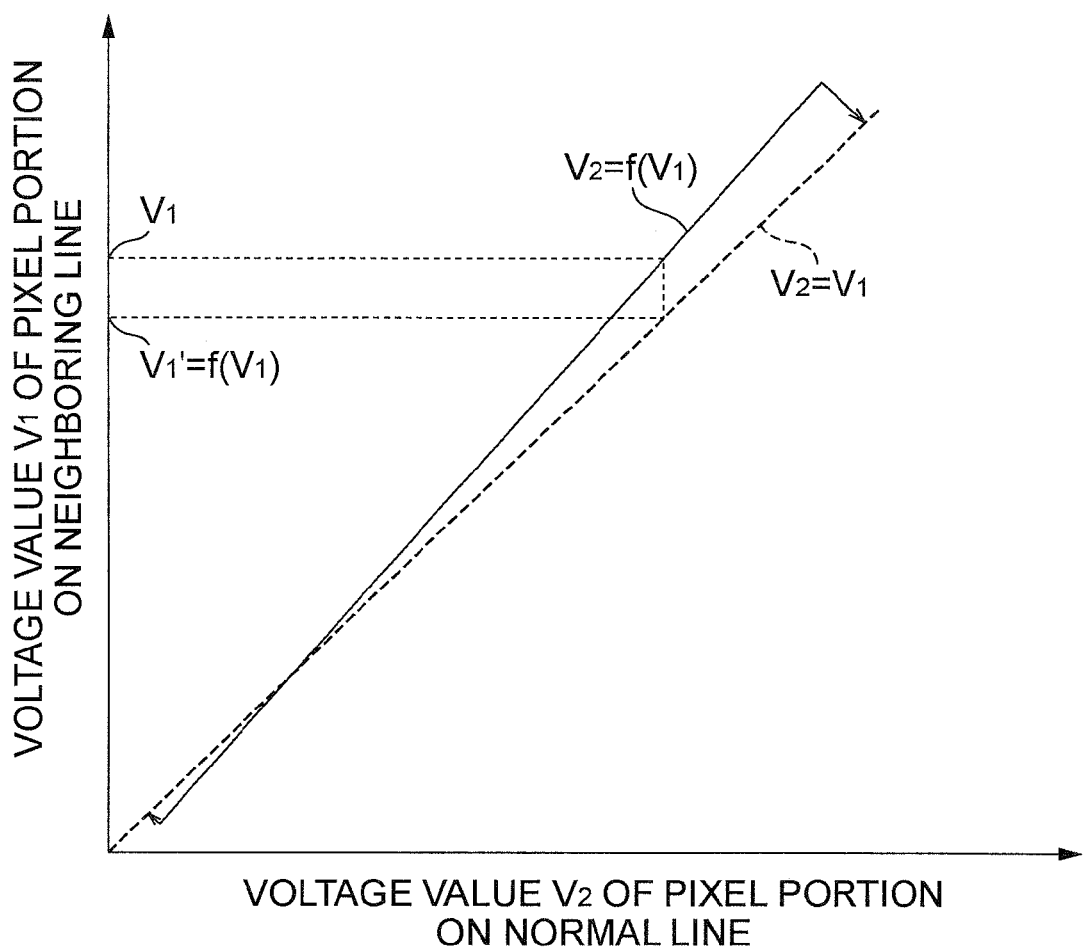
FIG. 4 is a graph showing a relationship between voltage values corresponding to pixel portions on a normal line and a neighboring line in frame data output from the signal reading-out section shown in FIG. 1.

FIG. 4 is a graph showing the relationship between voltage values corresponding to pixel portions on a normal line and a neighboring line in frame data outputted from the signal reading-out section shown in FIG. 1. In FIG. 4, light with uniform intensity is made incident on the entire photodetecting section 10. While changing this incident light intensity, the relationship between a voltage value $V_1$ corresponding to a pixel portion on a neighboring line and a voltage value $V_2$ corresponding to a pixel portion on a normal line is obtained. The relationship thus obtained is shown by a solid line. In FIG. 4, the line of "$V_2 = V_1$" is shown by a dashed line. These voltage values $V_1$ and $V_2$ are values after dark calibration. The normal line is neither a defective line the row selecting wiring of which is disconnected, nor a neighboring line into which charges flow from a pixel portion on the defective line.

As shown in FIG. 4, the voltage value $V_2$ corresponding to the pixel portion on the normal line is generally expressed as the following formula (1). This formula (1) is a function containing the voltage value $V_1$ corresponding to the pixel portion on the neighboring line as an input variable. It is simply expressed as the following formula (2). In this formula (2), the voltage value $V_2$ corresponding to the pixel portion on the normal line is expressed by, for example, a quartic polynomial containing the voltage value $V_1$ corresponding to the pixel portion on the neighboring line as an input variable.

In FIG. 4, light with uniform intensity is made incident on the entire photodetecting section 10, so that the voltage value $V_1$ corresponding to the pixel portion on the neighboring line should become equal to the voltage value $V_2$ corresponding to the pixel portion on the normal line unless inflow, etc., of charges from the pixel portion on the defective line occur. However, due to the inflow of charges from the pixel portion on the defective line, the voltage value $V_1$ becomes different from the voltage value $V_2$.

Here, formula (1) is defined as an expression which relates a voltage value $V_1$ corresponding to a pixel portion on a neighboring line and a voltage value $V_2$ corresponding to a pixel portion on a normal line when light with uniform intensity is made incident on the photodetecting section. In detail, for formula (2) which is a polynomial, coefficients a to e are determined at the time of inspection of the product. Specifically, when the voltage value $V_1$ is obtained in the pixel portion on the neighboring line, $V_2$ is obtained by substituting $V_1$ into the formula (2). Formulas (1) and (2) are expressions showing the relationship between voltage values outputted from pixel portions on the neighboring line and the normal line when light with uniform intensity is irradiated, and formula (3) is defined as an expression for obtaining a correction value $V_1'$ from the voltage value $V_1$ of the pixel portion on the neighboring line.

In detail, as shown in FIG. 4, the value $V_2$ which is obtained according to formula (1) (in detail, formula (2) with determined coefficients) when the voltage value corresponding to the pixel portion on the neighboring line is $V_1$ becomes the value of the voltage value $V_1$ corresponding to the pixel portion on the neighboring line in the case where inflow, etc., of charges from the pixel portion on the defective line does not occur. Therefore, this value $V_2$ is used as a correction value ($V_1'$).

That is, formulas (1) and (2) are considered as expressions which relate the voltage value of the neighboring line to the voltage value of the normal line, and the voltage value of the normal line is obtained from the voltage value of the neighboring line. Then, the obtained voltage value is set as the voltage value of the neighboring line when inflow, etc., of charges from the pixel portion on the defective line does not occur.

[Formula 1]

$$V_2 = f(V_1) \tag{1}$$

[Formula 2]

$$V_2 = aV_1^4 + bV_1^3 + cV_1^2 + dV_1 + e \tag{2}$$

Thus, the voltage value $V_1$ corresponding to the pixel portion $P_{m2,n1}$ on the neighboring line in frame data outputted from the signal reading-out section 20 is corrected by being converted according to the polynomial of formula (3) given below which contains the voltage value as an input variable. The correction processing section 40 determines the voltage value corresponding to the pixel portion $P_{m1,n1}$ on the defective line based on the voltage value $V_1'$ after correction.

[Formula 3]

$$V_1' = aV_1^4 + bV_1^3 + cV_1^2 + dV_1 + e \tag{3}$$

The correction processing section 40 preferably applies dark calibration in advance to the voltage values corresponding to pixel portions in the frame data outputted from the signal reading-out section 20 before the above-described processing. The correction processing section 40 may use analog processing to perform the above-described processing. Preferably, the correction processing section 40 performs digital processing after digitally converting the frame data outputted from the signal reading-out section 20, and in this case, preferably has frame memories which store frame data as digital values.

Preferably, in order to perform the above-described processing, the correction processing section 40 comprises a storage section which stores a disconnected row selecting wiring among the row selecting wirings $L_{V,1}$ to $L_{V,M}$ and a disconnection point of the disconnected row selecting wiring in advance. Further, disconnection information obtained in inspection in the middle of or after production of the solid-state imaging device 1 according to the first embodiment may be stored in the storage section from the outside.

The correction processing section 40 may be provided integrally with the photodetecting section 10, the signal reading-out section 20, and the controlling section 30. In this case, preferably, the entire solid-state imaging device 1 according to the first embodiment is integrated on a semiconductor substrate. While the photodetecting section 10, the signal reading-out section 20, and the controlling section 30 are integrated, the correction processing section 40 may be provided separately. In this case, the correction processing section 40 can be realized by, for example, a computer.

As described above, in the solid-state imaging device 1 according to the first embodiment or the method of correcting frame data outputted from the signal reading-out section 20 of the solid-state imaging device 1 (frame data correcting method according to the present invention), the voltage value corresponding to the pixel portion $P_{m2,n1}$ on the neighboring line in the frame data is corrected according to the function expression. That is, when correcting the voltage value corresponding to the pixel portion $P_{m2,n1}$ on the neighboring line, it is not necessary to use a voltage value corresponding to a pixel portion on a normal line. Therefore, in the first embodiment, the resolution near the defective line in the corrected image becomes higher than in the conventional technique described in Patent Document 1.

In the first embodiment, the frame data output operation by the signal reading-out section 20 and the correction processing by the correction processing section 40 may be performed alternately, or performed in parallel. In the former case, after an operation for outputting the frame data $F_k$ (frame data outputted k-th) by the signal reading-out section 20, correction processing for the frame data $F_k$ by the correction processing section 40 is performed, and after the correction processing is finished, the next frame data $F_{k+1}$ is outputted from the signal reading-out section 20 to the correction processing section 40. On the other hand, in the latter case, after the operation for outputting the frame data $F_k$ by the signal reading-out section 20, the correction processing for the frame data $F_k$ by the correction processing section 40 is performed, and in a period at least a part of which overlaps the period of the correction processing, the next frame data $F_{k+1}$ is outputted from the signal reading-out section 20 to the correction processing section 40.

The leakage of charges from a pixel portion on a defective line to a pixel portion on a neighboring line occurs so that the charges leak to pixel portions on neighboring lines on both sides of the defective line. Therefore, preferably, the pixel portions on neighboring lines on both sides of the defective line are subjected to the frame data correction according to the present invention. However, in a case where a voltage value of a pixel portion on a neighboring line on one side of the defective line and a voltage value of a pixel portion on a normal line further neighboring the neighboring line on the same side are binned (summed) and reading-out, the frame data correction according to the present invention is applied to only the voltage value of the pixel portion on the neighboring line on the other side of the defective line. Even in this case, a resolution higher than in the conventional technique described in Patent Document 1 is obtained.

Second Embodiment

Figure 5:
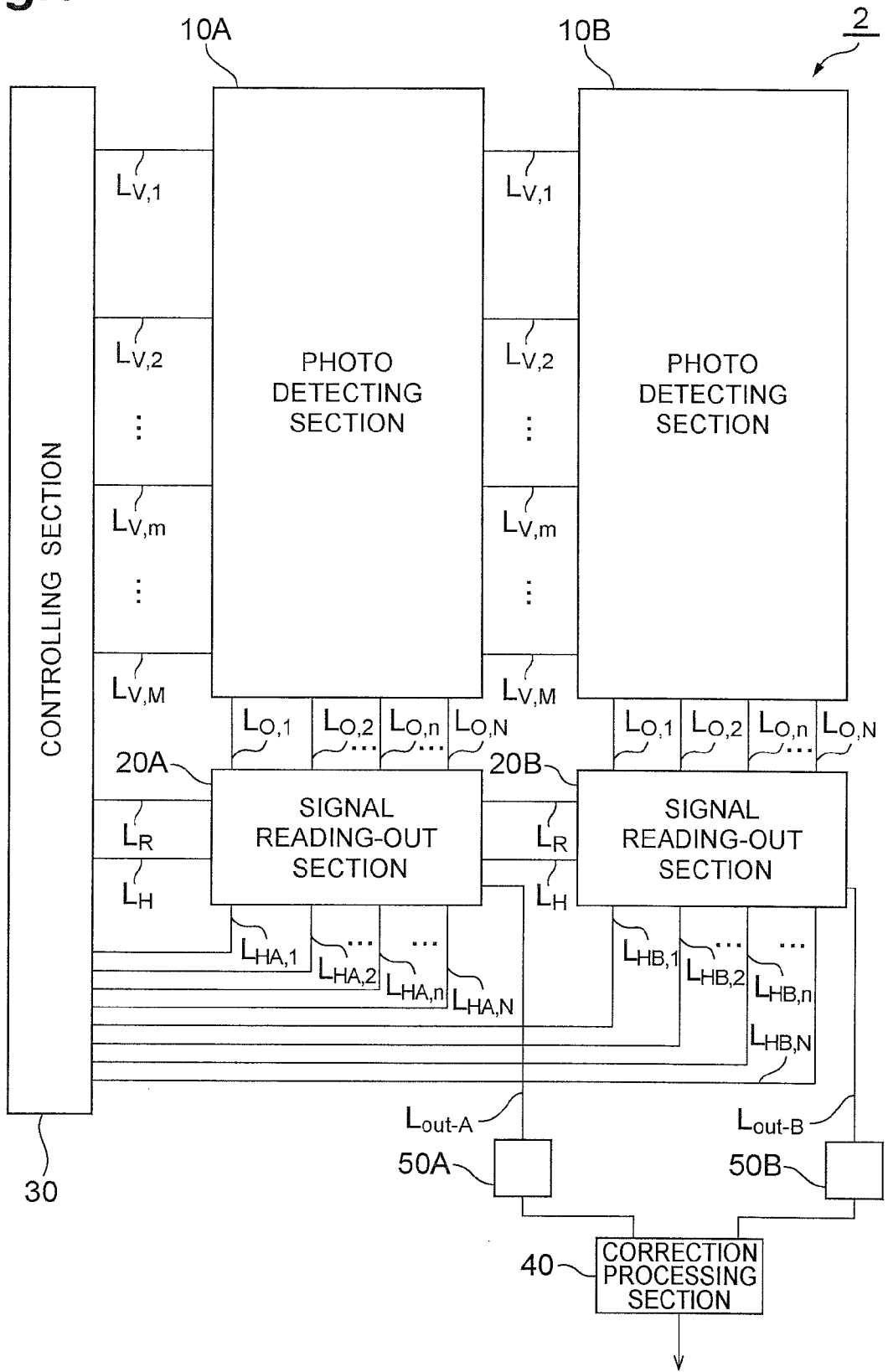
FIG. 5 is a view showing a configuration of a second embodiment of the solid-state imaging device according to the present invention.

Next, a second embodiment of the solid-state imaging device according to the present invention will be described. FIG. 5 is a view showing a configuration of the second embodiment of a solid-state imaging device according to the present invention. This solid-state imaging device 2 according to the second embodiment comprises photodetecting sections 10A and 10B, signal reading-out sections 20A and 20B, a controlling section 30, a correction processing section 40, and buffer sections 50A and 50B. When it is used as an X-ray flat panel, a scintillator panel is overlaid on the photodetecting surfaces 10A and 10B of the solid-state imaging device 2.

The photodetecting sections 10A and 10B constituting a part of the solid-state imaging device 2 according to the second embodiment have a structure similar to that of the photodetecting section 10 included in the solid-state imaging device 1 according to the first embodiment. The signal reading-out sections 20A and 20B constituting a part of the solid-state imaging device 2 according to the second embodiment also have a structure similar to that of the signal reading-out section 20 included in the solid-state imaging device 1 according to the first embodiment.

The controlling section 30 included in the solid-state imaging device 2 outputs an m-th row selecting controlling signal Vsel(m) to the m-th row selecting wiring $L_{V,m}$ to supply this m-th row selecting controlling signal Vsel(m) to the pixel portions $P_{m,1}$ to $P_{m,N}$ belonging to the m-th rows included in the photodetecting sections 10A and 10B. The controlling section 30 outputs an n-th column selecting controlling signal Hsel(n) which should be supplied to each holding circuit $H_n$ included in the signal reading-out section 20A to the n-th column selecting wiring $L_{HA,n}$, and outputs an n-th column selecting controlling signal Hsel(n) which should be supplied to each holding circuit $H_n$ included in the signal reading-out section 20B to the n-th column selecting wiring $L_{HB,n}$.

The controlling section 30 outputs a discharge controlling signal Reset which should be supplied to the respective integrating circuits $S_n$ included in the signal reading-out sections 20A and 20B to the discharge controlling wiring $L_R$. The controlling section 30 outputs a hold controlling signal Hold which should be supplied to the respective holding circuits $H_n$ included in the signal reading-out sections 20A and 20B to the hold controlling wiring $L_H$.

As described above, the controlling section 30 controls opening and closing operations of the reading-out switches $SW_1$ included in N pixel portions $P_{m,1}$ to $P_{m,N}$ belonging to the m-th rows included in the photodetecting sections 10A and 10B, and controls voltage value holding operations and output operations in the signal reading-out sections 20A and 20B. Accordingly, the controlling section 30 makes the signal reading-out sections 20A and 20B repeatedly output voltage values corresponding to amounts of charges generated in the photodiodes PD included in M×N pixel portions $P_{1,1}$ to $P_{M,N}$ in the photodetecting sections 10A and 10B as frame data.

Thus, the solid-state imaging device 2 according to the second embodiment comprises a plurality of pairs of photodetecting sections and signal reading-out sections (sensor elements), and accordingly, the solid-state imaging device can expand the photodetecting region, or increase the number of pixels. In the solid-state imaging device 2 according to the second embodiment, the plurality of signal reading-out sections can be operated in parallel to each other, and high-speed reading out of pixel data is possible.

The buffer sections serve as signal output sections for transmitting signals from any one of the plurality of pairs of sensor elements (each including at least a photodetecting section and a signal reading-out section) to the correction processing section, respectively. The pairs of photodetecting sections and signal reading-out sections can be formed on semiconductor substrates different from each other, and in this case, the correction processing section can be formed on any semiconductor substrate on which the photodetecting section and the signal reading-out section are formed, or still another semiconductor substrate. The buffer section may consist of only a buffer amplifier.

The correction processing section 40 inputs voltage values which were successively outputted from the holding circuits $H_n$ included in the signal reading-out section 20A to the voltage output wiring $L_{out\_A}$ and passed through the buffer section 50A, and inputs voltage values which were successively outputted from the holding circuits $H_n$ included in the signal reading-out section 20B to the voltage output wiring $L_{out\_A}$ and passed through the buffer section 50B. Then, the correction processing section 40 applies correction processing to frame data repeatedly outputted from the signal reading-out sections 20A and 20B, and outputs frame data after correction processing.

The details of processing in the correction processing section 40 are as described above. However, the operation characteristics of the buffer section 50A and the buffer section 50B are not always equal to each other, and even when their input voltage values are the same, their output voltage values are different in some cases. Therefore, when a row selecting wiring of any one of the rows included in the photodetecting section 20A is disconnected, it is preferable that coefficients a to e determined based on incident light intensity dependencies of voltage values corresponding to a pixel portion (normal line) which is neither a pixel portion $P_{m1,n1}$ nor a pixel portion $P_{m2,n1}$ included in the photodetecting section 20A and incident light intensity dependencies of voltage values corresponding to the pixel portion $P_{m2,n1}$ (neighboring line) are used.

Similarly, in the correction processing section 40, when a row selecting wiring of any one of the rows included in the photodetecting section 20B is disconnected, it is preferable that coefficients a to e determined based on incident light intensity dependencies of voltage values corresponding to a pixel portion (normal line) which is neither a pixel portion $P_{m1,n1}$ nor a pixel portion $P_{m2,n1}$ included in the photodetecting section 20B and incident light intensity dependencies of voltage values corresponding to the pixel portion $P_{m2,n1}$ (neighboring line) are used.

X-Ray CT Apparatus

The solid-state imaging device 1 according to the first embodiment or the method of correcting frame data outputted from the signal reading-out section 20 of the solid-state imaging device 1 (frame data correcting method according to the present invention) is preferably used in an X-ray CT apparatus. An embodiment of an X-ray CT apparatus including the solid-state imaging device 1 according to the first embodiment will be described next.

Figure 6:
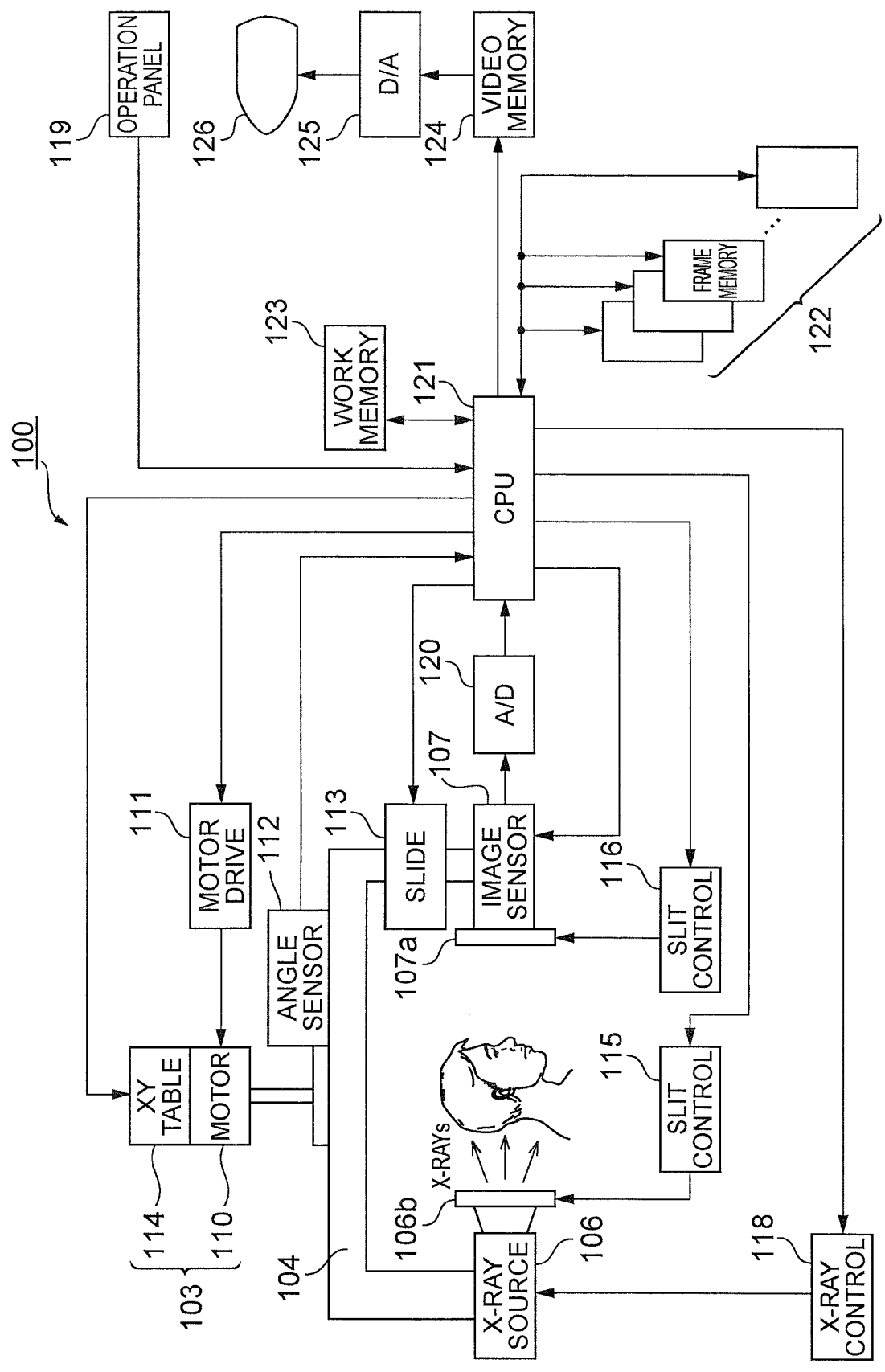
FIG. 6 is a view showing a configuration of an embodiment of an X-ray CT apparatus according to the present invention.

FIG. 6 is a view showing a configuration of an embodiment of an X-ray CT apparatus according to the present invention. In the X-ray CT apparatus 100 shown in FIG. 6, an X-ray source 106 generates X-rays toward a subject. The radiation field of the X-rays generated from the X-ray source 106 is controlled by a primary slit plate 106b. The X-ray source 106 includes an X-ray tube installed inside, and by adjusting the conditions such as a tube voltage, a tube current, and an energization time of the X-ray tube, the X-ray irradiation amount onto the subject is controlled. An X-ray imaging sensor 107 includes a CMOS solid-state imaging device having a plurality of pixel portions two-dimensionally arrayed, and detects an X-ray image which passed through the subject. In front of the X-ray imaging sensor 107, a secondary slit plate 107a which limits an X-ray incidence region is provided.

A swing arm 104 swings the X-ray source 106 and the X-ray imaging sensor 107 around a subject while holding these opposite to each other when performing panoramic tomography. The swing arm 104 is provided with a slide mechanism 113 for linearly displacing the X-ray imaging sensor 107 with respect to a subject when performing linear tomography. The swing arm 104 is driven by an arm motor 110 constituting a rotary table, and the rotation angle is detected by an angle sensor 112. The arm motor 110 is loaded on a movable portion of an XY table 114, and the rotation center is arbitrarily adjusted within the horizontal plane.

An image signal outputted from the X-ray imaging sensor 107 is converted into digital data of, for example, 10 bits (=1024 level) by an AD converter 120, and temporarily taken into a CPU (Central Processing Unit) 121. Then, the digital data is stored in a frame memory 122. From the image data stored in the frame memory 122, a tomographic image along an arbitrary tomographic surface is reproduced by predetermined arithmetic processing. The reproduced tomographic image is outputted to a video memory 124, converted into an analog signal by a DA converter 125, and then displayed by an image display section 126 such as a CRT (Cathode-Ray Tube) (and used for various diagnoses).

To the CPU 121, a work memory 123 necessary for signal processing is connected, and further, an operation panel 119 including a panel switch and an X-ray irradiation switch, etc., is connected. The CPU 121 is connected to a motor driving circuit 111 which drives the arm motor 110, slit control circuits 115 and 116 which control aperture ranges of the primary slit plate 106b and the secondary slit plate 107a, and an X-ray control circuit 118 which controls the X-ray source 106, and further, outputs a clock signal for driving the X-ray imaging sensor 107.

The X-ray control circuit 118 can feedback-control the X-ray irradiation amount onto a subject based on a signal imaged by the X-ray imaging sensor 107.

In the X-ray CT apparatus 100 configured as described above, the X-ray imaging sensor 107 is equivalent to the photodetecting section 10, the signal reading-out section 20, and the controlling section 30 of the solid-state imaging device 1 according to the first embodiment, and a scintillator panel is provided on the front surface of the photodetecting section 10. The CPU 121 and the work memory 123 are equivalent to the correction processing section 40 of the solid-state imaging device 1 according to the first embodiment.

The X-ray CT apparatus 100 includes the solid-state imaging device 1 according to the first embodiment, and includes the CPU 121 as an image analyzing section which generates a tomographic image of a subject based on frame data after correction processing outputted from the solid-state imaging device 1. With this configuration, the X-ray CT apparatus 100 can obtain a tomographic image with high resolution near a defective line. Particularly, in the X-ray CT apparatus 100, multiple (for example, 300) frame data is continuously acquired in a short period, and the incident light amount onto the photodetecting section 10 of the solid-state imaging device 1 changes by frame, so that the amount of charges which overflow from a pixel portion on a defective line to a pixel portion on a neighboring line changes by frame. In this X-ray CT apparatus 100, by providing the solid-state imaging device 1, effective correction can be applied to frame data. The X-ray CT apparatus 100 may include the solid-state imaging device 2 according to the second embodiment instead of the solid-state imaging device 1 according to the first embodiment.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

The invention claimed is:

1. A solid-state imaging device, comprising:
   a photodetecting section having M×N pixel portions $P_{1,1}$ to $P_{M,N}$ two-dimensionally arrayed so as to constitute a matrix with M (integer not less than 2) rows and N (integer not less than 2) columns, each of the pixel portions $P_{1,1}$ to $P_{M,N}$ including a photodiode which generates charges of an amount corresponding to an incident light intensity, and a reading-out switch connected to the photodiode;
   a reading-out wiring $L_{O,n}$ being connected to reading-out switches included in M pixel portions $P_{1,n}$ to $P_{M,n}$ belonging to the n(integer not less than 1 and not more than N)-th column in the photodetecting section, the reading-out wiring reading out charges generated in a photodiode included in any one of the pixel portions $P_{1,n}$ to $P_{M,n}$ via a corresponding reading-out switch;
   a signal reading-out section being connected to the reading-out wirings $L_{O,1}$ to $L_{O,N}$, the signal reading-out section temporarily holding voltage values corresponding to amounts of charges inputted through the reading-out wirings $L_{O,n}$ and then successively outputting the held voltage values;
   a controlling section controlling a voltage value output operation in the signal reading-out section by controlling opening and closing operations of the reading-out switches included in N pixel portions $P_{m,1}$ to $P_{m,N}$ belonging to the m(integer not less than 1 and not more than M)-th row in the photodetecting section, the controlling section making the signal reading-out section repeatedly output voltage values corresponding to amounts of charges generated in photodiodes included in the M×N pixel portions $P_{1,1}$ to $P_{M,N}$ in the photodetecting section as frame data;
   a row selecting wiring $L_{V,m}$ being connected to reading-out switches included in N pixel portions $P_{m,1}$ to $P_{m,N}$ belonging to the m-th row in the photodetecting section, the row selecting wiring transmitting a signal for controlling opening and closing operations of the reading-out switches from the controlling section to the reading-out switches; and
   a correction processing section applying correction processing to frame data repeatedly outputted from the signal reading-out section,
   wherein, when a pixel portion disconnected from the controlling section due to disconnection of the m1(integer not less than 1 and not more than M)-th row selecting wiring $L_{V,m}$ among the row selecting wirings $L_{V,1}$ to $L_{V,m}$ is defined as a pixel portion $P_{m1,n1}$, and a pixel portion neighboring the pixel portion $P_{m1,n1}$ and belonging to the m2(integer not less than 1 and not more than M)-th row neighboring the m1-th row is defined as a pixel portion $P_{m2,n1}$ the correction processing section:

corrects a voltage value corresponding to the neighboring pixel portion $P_{m2,n1}$ in frame data outputted from the signal reading-out section by converting the voltage value in accordance with a function expression with the voltage value as an input variable, and determines, after correcting the voltage value corresponding to the neighboring pixel portion $P_{m2,n1}$, a voltage value corresponding to the pixel portion $P_{m1,n1}$ in the frame data based on the corrected value of the voltage value corresponding to the neighboring pixel portion $P_{m2,n1}$.

2. The solid-state imaging device according to claim 1, wherein the correction processing section uses a polynomial as the function expression, and uses values determined based on incident light intensity dependency of voltage value corresponding to a pixel portion which is neither the pixel portion $P_{m1,n1}$ nor the neighboring pixel portion $P_{m2,n1}$ and incident light intensity dependency of voltage value corresponding to the neighboring pixel portion $P_{m2,n1}$, as coefficients of the polynomial.

3. The solid-state imaging device according to claim 2, wherein the correction processing section corrects the voltage value corresponding to the neighboring pixel portion $P_{m2,n1}$ in the frame data by setting the coefficients for each of any plurality of row selecting wirings among the row selecting wirings $L_{V,1}$ to $L_{V,M}$ when the plurality of row selecting wirings are disconnected.

4. The solid-state imaging device according to claim 2, wherein when the photodetecting section, the reading-out wiring $L_{O,n}$, the signal reading-out section, and the row selecting wiring $L_{V,m}$ constitute one sensor element, the solid-state imaging device comprises a plurality of sensor elements each having the same structure as that of the sensor element, and wherein, when any one of the row selecting wirings included in any one of the plurality of sensor elements is disconnected, the correction processing section determines the coefficients based on incident light intensity dependency of voltage value corresponding to a pixel portion which is neither the pixel portion $P_{m1,n1}$ nor the neighboring pixel portion $P_{m2,n1}$ and incident light intensity dependency of voltage value corresponding to the pixel portion $P_{m2,n1}$ in the sensor element including the disconnected row selecting wiring.

5. An X-ray CT apparatus, comprising:

an X-ray output section which outputs X-rays toward a subject;

the solid-state imaging device according to claim 1 which images the subject by receiving X-rays reaching from the X-ray output section through the subject;

moving means for moving the X-ray output section and the solid-state imaging device relative to the subject; and an image analyzing section inputting frame data after correction processing outputted from the solid-state imaging device and generating a tomographic image of the subject based on the frame data.

6. A frame data correcting method of correcting frame data outputted from a solid-state imaging device which includes:

a photodetecting section having M×N pixel portions $P_{1,1}$ to $P_{M,N}$ two-dimensionally arrayed so as to constitute a matrix with M (integer not less than 2) rows and N (integer not less than 2) columns, each of the pixel portions $P_{1,1}$ to $P_{M,N}$ including a photodiode which generates charges of an amount corresponding to an incident light intensity, and a reading-out switch connected to the photodiode;

a reading-out wiring $L_{O,n}$ being connected to reading-out switches included in M pixel portions $P_{1,n}$ to $P_{M,n}$ belonging to the n(integer not less than 1 and not more than N)-th column in the photodetecting section, the reading-out wiring reading out charges generated in a photodiode included in any one of the pixel portions $P_{1,n}$ to $P_{M,n}$ via a corresponding reading-out switch;

a signal reading-out section being connected to the reading-out wirings $L_{O,1}$ to $L_{O,N}$, the signal reading-out section temporarily holding voltage values corresponding to amounts of charges inputted through the reading-out wirings $L_{O,n}$ and then successively outputting the held voltage values;

a controlling section controlling a voltage value output operation in the signal reading-out section by controlling opening and closing operations of the reading-out switches included in N pixel portions $P_{m,1}$ to $P_{m,N}$ belonging to the m(integer not less than 1 and not more than M)-th row in the photodetecting section, the controlling section making the signal reading-out section repeatedly output voltage values corresponding to amounts of charges generated in photodiodes included in the M×N pixel portions $P_{1,1}$ to $P_{M,N}$ in the photodetecting section as frame data; and a row selecting wiring $L_{V,m}$ being connected to the reading-out switches included in N pixel portions $P_{m,1}$ to $P_{m,N}$ belonging to the m-th row in the photodetecting section, the row selecting wiring transmitting a signal for controlling opening and closing operations of the reading-out switches from the controlling section to the reading-out switches, the frame data correcting method comprises the steps of:

when a pixel portion disconnected from the controlling section due to disconnection of the m1(integer not less than 1 and not more than M)-th row selecting wiring $L_{V,m}$, among the row selecting wirings $L_{v,1}$ to $L_{V,m}$ is defined as a pixel portion $P_{m1,n1}$, and a pixel portion neighboring the pixel portion $P_{m1,n1}$ and belonging to the m2(integer not less than 1 and not more than M)-th row neighboring the m1-th row is defined as a pixel portion $P_{m2,n1}$, correcting a voltage value corresponding to the neighboring pixel portion $P_{m2,n1}$ in frame data outputted from the signal reading-out section by converting the voltage value in accordance with a function expression with the voltage value as an input variable; and determining, after correcting the voltage value corresponding to the neighboring pixel portion $P_{m2,n1}$, a voltage value corresponding to the pixel portion $P_{m1,n1}$ in the frame data, on the basis of the corrected value of the voltage value corresponding to the neighboring pixel portion $P_{m2,n1}$.

7. The frame data correcting method according to claim 6, wherein values determined based on incident light intensity dependency of voltage value corresponding to a pixel portion which is neither the pixel portion $P_{m1,n1}$ nor the neighboring pixel portion $P_{m2,n1}$ and incident light intensity dependency of voltage value corresponding to the neighboring pixel portion $P_{m2,n1}$, are used as coefficients of a polynomial as the function expression.

8. The frame data correcting method according to claim 7, wherein the voltage value corresponding to the neighboring pixel portion $P_{m2,n1}$ in the frame data is corrected by setting the coefficients for each of any plurality of row selecting wirings among the row selecting wirings $L_{V,1}$ to $L_{V,M}$ when the plurality of row selecting wirings are disconnected.

9. The frame data correcting method according to claim 7, wherein, when the photodetecting section, the reading-out wiring $L_{O,n}$, the signal reading-out section, and the row selecting wiring $L_{V,m}$ constitute one sensor element, the solid-state imaging device includes a plurality of sensor elements each having the same structure as that of the sensor element, and wherein, when any one of the row selecting wirings included in any one of the plurality of sensor elements is disconnected, the coefficients are obtained based on incident light intensity dependency of voltage value corresponding to a pixel portion which is neither the pixel portion $P_{m1,n1}$ nor the neighboring pixel portion $P_{m2,n1}$ and incident light intensity dependency of voltage value corresponding to the neighboring pixel portion $P_{m2,n1}$ in the sensor element including the disconnected row selecting wiring.

* * * * *

UNITED STATES PATENT AND TRADEMARK OFFICE
CERTIFICATE OF CORRECTION

PATENT NO.        : 8,547,464 B2
APPLICATION NO.   : 12/864134
DATED             : October 1, 2013
INVENTOR(S)       : Kyushima et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this
Fifteenth Day of September, 2015

Michelle K. Lee
*Director of the United States Patent and Trademark Office*